(12) United States Patent
Levin (10) Patent No.: US 7,432,243 B2
(45) Date of Patent: Oct. 7, 2008

(54) TRUNCATED 24KDA BASIC FIBROBLAST GROWTH FACTOR

(75) Inventor: Eugene G. Levin, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 558 days.

(21) Appl. No.: 10/408,415

(22) Filed: Apr. 7, 2003

(65) Prior Publication Data

US 2003/0220256 A1    Nov. 27, 2003

Related U.S. Application Data

(60) Provisional application No. 60/370,212, filed on Apr. 8, 2002.

(51) Int. Cl.
| | |
|---|---|
| A61K 38/18 | (2006.01) |
| C07K 17/00 | (2006.01) |
| C07K 14/50 | (2006.01) |
| C07K 19/00 | (2006.01) |

(52) U.S. Cl. ................ 514/12; 530/324; 930/280

(58) Field of Classification Search ............ None
See application file for complete search history.

(56) References Cited

U.S. PATENT DOCUMENTS

| | | | | |
|---|---|---|---|---|
| 5,478,740 | A * | 12/1995 | Iwane et al. | 435/336 |
| 6,440,934 | B1 * | 8/2002 | Whitehouse | 514/12 |
| 2003/0008820 | A1 * | 1/2003 | Kwan et al. | 514/12 |

FOREIGN PATENT DOCUMENTS

| | | | |
|---|---|---|---|
| WO | WO 94/00570 | | 1/1994 |
| WO | WO 01/12236 | * | 2/2001 |
| WO | WO 01/98346 | | 12/2001 |

OTHER PUBLICATIONS

Fraser et al. Suppression of luteal angiogenesis in the primate after neutralization of vascular endothelial growth factor. Endocrinology. Mar. 2000;141(3):995-1000.*

Bowie et al. Deciphering the message in protein sequences: tolerance to amino acid substitutions. Science, (Mar. 16, 1990) 247 (4948) 1306-10.*

Ngo et al., in The Protein Folding Problem and Tertiary Structure Prediction, Merz and Le Grand (Eds), Aug. 1994, Springer Verlag, pp. 492-495.*

Janknecht et al. Affinity purification of histidine-tagged proteins transiently produced in HeLa cells. Gene. Nov. 16, 1992;121(2):321-4.*

Jaine et al., Vessels of Death or Life, Sci. Am., pp. 38-45 (2001).

Wulff et al., J. Clin. Endocrinol Metab., 86(7):3377-3386 (2001).

Randolph et al., J. Cellular Physiology, 178:144-153 (1999).

Piotrowicz et al., J. Biological Chemistry, 276(6):3963-3970 (2001).

Ding et al., J. Biological Chemistry, 277(34):31056-31061 (2002).

Piotrowicz Randolph S et al., "Dual activities of 22-24 kDa basic fibroblast growth factor: Inhibition of migration and stimulation of proliferation," Journal of Cellular Physiology, vol. 178, No. 2, Feb. 1999, pp. 144-153.

Piotrowicz Randolph S et al., "The 27-kDa heat shock protein facilities basic fibroblast growth factor release from endothelial cells," Journal of Biological Chemistry, vol. 272, No. 11, 1997, pp. 7042-7047.

Piotrowicz Randolph S et al., "Inhibition of cell migration by 24-kDa fibroblast growth factor-2 is dependent upon the estrogen receptor," The Journal of Biological Chemistry. Feb. 9, 2001, vol. 276, No. 6, pp. 3963-3970.

Yi M et al., "A fibronectin fragment inhibits tumor growth, angiogenesis, and metastasis," Proceedings of the National Academy of Sciences of The United States, National Academy of Science. Washington, DC, US, vol. 98, No. 2, Jan. 16, 2001, pp. 620-624.

Levin Eugene G et al., "Suppression of tumor growth and angiogenesis in vivo by a truncated form of 24-kd fibroblast growth factor (FGF)-2," American Journal of Pathology, vol. 164, No. 4, Apr. 2004, pp. 1183-1190.

* cited by examiner

*Primary Examiner*—David S Romeo
(74) *Attorney, Agent, or Firm*—T D Foster; M. Reza Savari (57) ABSTRACT

The invention relates to fragments of an amino acid sequence of mature, full length 24 kDa fibroblast growth factor-2 or an analog thereof. The fragments have an activity that inhibits the migration of cultured cells as well as inhibiting angiogenesis, tumor growth, or any other processes that involve the migration of cells in vivo. This fragment does not stimulate the proliferation of cells which is in contrast to activity shown by the mature, full-length 24 kDa fibroblast growth factor-2. The present invention also relates to a DNA molecule encoding the fragment, an expression vector and a transformed host containing the DNA molecule, and a method of producing the protein by culturing the transformed host. Moreover, the present invention relates to a therapeutic composition the 24 kDa fibroblast growth factor fragment and a pharmaceutically acceptable carrier.

8 Claims, 10 Drawing Sheets

PEPTIDE SEQUENCE OF 24kD FGF-2

LGDRGRGRALPGGRLGGRGR GRAPERVGGR GRGRGTAAPRAAPAARASRPGPA GT
MAAGS ITTLPALPEDGGSGAFPPGHFKDPKRLYCKNGGFFLRIHPDGRVDGV
REKSDPHIKLQLQAEERGVVSIKGVCANRYLAMKEDGRLLASKCVTDECFFFERL
ESNNYNTYRSRKYTSWYVALKRTGQYKLGSKTGPGQKAILFLPMSAKS cDNA sequence of 24kD FGF-2

```
ctggggga    ccgcgggcgc  ggccgcgcgc  tgccgggcgg  gaggctgggg  ggccggggcc
ggggccgtgc  cccggagcgg  gtcggaggcc  ggggccgggg  ccggggggacg  gcggctcccc
gcgcggctcc  agcggctcgg  ggatcccggc  cgggccccgc  agggaccatg  gcagccggga
gcatcaccac  gctgcccgcc  ttgcccgagg  atggcggcag  cggcgccttc  ccgccggcc
acttcaagga  ccccaagcgg  ctgtactgca  aaaacggggg  cttcttcctg  cgcatccacc
ccgacggccg  agttgacggg  gtccgggaga  gagcgaccc  tcacatcaag  ctacaacttc
aagcagaaga  gagaggagtt  gtgtctatca  aaggagtgtg  tgctaaccgt  tacctggcta
tgaaggaaga  tggaagatta  ctggcttcta  aatgttac    ggatgagtgt  ttcttttttg
aacgattgga  atctaataac  tacaatactt  accggtcaag  gaaatacacc  agttggtatg
tggcactgaa  acgaactggg  cagtataaac  ttggatccaa  aacaggacct  gggcagaaag
ctatactttt  tcttccaatg  tctgctaaga  gctga
```

1
LGD*RGRGR*

2
ALPGG*R*LGG*RGRGR*

3
APE*R*VGG*RGRG*RGT

4
AAP*R*AAPAA*R*AS*R*PGPAGT M—30 amino acids

FIGURE 7A AND B

Amino Acid Sequence of Full Length 24kD FGF-2

LGDRGRGRAL PGGRLGGRGR GRAPERVGGR GRGRGTAAPR AAPA
ARASRP GPAGTAAAGS ITTLP ALPED GGSGA FPPGH FKDPK
RLYCKNGGFFLRIHPDGRVDGVREKSDPHIKLQLQAEERGVVSIKGVCANRYLA
MKEDGRLLASKCVTDECFFFERLESNNYNTYRSRKYTSWYVALKRTGQYKLGS
KTGPGQKAILFLPMSAKS (SEQ ID NO: 1)

FIGURE 8A

Amino Acid Sequence of ATE+31

LGDRGRGRALPGGRLGGRGRGRAPERVGGRGRGRGTAAPRAAPAARASRPGPA
GTAAAGSITTLPALPEDGGSGAFPPGHFKDPKR (SEQ ID NO: 2)

FIGURE 8B

Amino Acid Sequence of ATE+33

LGDRGRGRALPGGRLGGRGRGRAPERVGGRGRGRGTAAPRAAPAARASRPGPA
GTAAAGSITTLPALPEDGGSGAFPPGHFKDPKRLY (SEQ ID NO: 3)

FIGURE 8C

Nucleic Acid Sequence of Full Length 24kD FGF-2 ctgggggac cgcgggcgcg gccgcgcgct gccgggcggg aggctggggg gccggggccg
gggccgtgcc ccggagcggg tcggaggccg gggccggggc cggggacgg cggctccccg
cgcggctcca gcggctcggg gatcccggcc gggccccgca gggaccgctg cagccgggag
catcaccacg ctgcccgcct tgcccgagga tggcggcagc ggcgccttcc cgcccggcca
cttcaaggac cccaagcggc tgtactgcaa aaacggggc ttcttcctgc gcatccaccc
cgacggccga gttgacgggg tccgggagaa gagcgaccct cacatcaagc tacaacttca
agcagaagag agaggagttg tgtctatcaa aggagtgtgt gctaaccgtt acctggctat
gaaggaagat ggaagattac tggcttctaa atgtgttacg gatgagtgtt tcttttttga
acgattggaa tctaataact acaatactta ccggtcaagg aaatacacca gttggtatgt
ggcactgaaa cgaactgggc agtataaact tggatccaaa acaggacctg ggcagaaagc
tatactttt cttccaatgt ctgctaagagc (SEQ ID NO: 4)

FIGURE 9A

Nuclei Acid Sequence of ATE+31 ctg ggg gac cgc ggg cgc ggc cgc gcg ctg ccg ggc ggg agg ctg ggg ggc cgg ggc cgg ggc
cgt gcc ccg gag cgg gtc gga ggc cgg ggc cgg ggc cgg ggg acg gcg gct ccc cgc gcg gct cca
gcg gct cgg gga tcc cgg ccg ggc ccc gca ggg acc gct gca gcc ggg agc atc acc acg ctg ccc
gcc ttg ccc gag gat ggc ggc agc ggcgcc ttc ccg ccc ggc cac ttc aag gac ccc aag cgg (SEQ ID NO: 5)

FIGURE 9B

Nucleic Acid Sequence of ATE+33 ctg ggg gac cgc ggg cgc ggc cgc gcg ctg ccg ggc ggg agg ctg ggg ggc cgg ggc cgg ggc
cgt gcc ccg gag cgg gtc gga ggc cgg ggc cgg ggc cgg ggg acg gcg gct ccc cgc gcg gct cca
gcg gct cgg gga tcc cgg ccg ggc ccc gca ggg acc gct gca gcc ggg agc atc acc acg ctg ccc
gcc ttg ccc gag gat ggc ggc agc ggc gcc ttc ccg ccc ggc cac ttc aag gac ccc aag cgg ctg tac (SEQ ID NO: 6)

SEQUENCE LISTING

<160> NUMBER OF SEQ ID NOS: 6

<210> SEQ ID NO 1
<211> LENGTH: 210
<212> TYPE: PRT
<213> ORGANISM: Human

<400> SEQUENCE: 1

```
Leu Gly Asp Arg Gly Arg Gly Arg Ala Leu Pro Gly Gly Arg Leu Gly
1               5                   10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Ala Ser
        35                  40                  45

Arg Pro Gly Pro Ala Gly Thr Ala Ala Ala Gly Ser Ile Thr Thr Leu
    50                  55                  60

Pro Ala Leu Pro Glu Asp Gly Gly Ser Gly Ala Phe Pro Pro Gly His
65                  70                  75                  80

Phe Lys Asp Pro Lys Arg Leu Tyr Cys Lys Asn Gly Gly Phe Phe Leu
                85                  90                  95

Arg Ile His Pro Asp Gly Arg Val Asp Gly Val Arg Glu Lys Ser Asp
            100                 105                 110

Pro His Ile Lys Leu Gln Leu Gln Ala Glu Glu Arg Gly Val Val Ser
        115                 120                 125

Ile Lys Gly Val Cys Ala Asn Arg Tyr Leu Ala Met Lys Glu Asp Gly
    130                 135                 140

Arg Leu Leu Ala Ser Lys Cys Val Thr Asp Glu Cys Phe Phe Phe Glu
145                 150                 155                 160

Arg Leu Glu Ser Asn Asn Tyr Asn Thr Tyr Arg Ser Arg Lys Tyr Thr
                165                 170                 175

Ser Trp Tyr Val Ala Leu Lys Arg Thr Gly Gln Tyr Lys Leu Gly Ser
            180                 185                 190

Lys Thr Gly Pro Gly Gln Lys Ala Ile Leu Phe Leu Pro Met Ser Ala
        195                 200                 205

Lys Ser
    210
```

<210> SEQ ID NO 2
<211> LENGTH: 86
<212> TYPE: PRT
<213> ORGANISM: Human

<400> SEQUENCE: 2

```
Leu Gly Asp Arg Gly Arg Gly Arg Ala Leu Pro Gly Gly Arg Leu Gly
1               5                   10                  15
```

Gly Arg Gly Arg Gly Arg Ala Pro Glu Arg Val Gly Arg Gly Arg
            20                  25                  30

Gly Arg Gly Thr Ala Ala Pro Arg Ala Ala Pro Ala Ala Arg Ala Ser
            35                  40                  45

Arg Pro Gly Pro Ala Gly Thr Ala Ala Ala Gly Ser Ile Thr Thr Leu
        50                  55                  60

Pro Ala Leu Pro Glu Asp Gly Gly Ser Gly Ala Phe Pro Pro Gly His
65                  70                  75                  80

Phe Lys Asp Pro Lys Arg
                85

<210> SEQ ID NO 3
<211> LENGTH: 88
<212> TYPE: PRT
<213> ORGANISM: Human

<400> SEQUENCE: 3

Leu Gly Asp Arg Gly Arg Gly Arg Ala Leu Pro Gly Gly Arg Leu Gly
1               5                   10                  15

Gly Arg Gly Arg Gly Arg Ala Pro Glu Arg Val Gly Arg Gly Arg
            20                  25                  30

Gly Arg Gly Thr Ala Ala Pro Arg Ala Ala Pro Ala Ala Arg Ala Ser
            35                  40                  45

Arg Pro Gly Pro Ala Gly Thr Ala Ala Ala Gly Ser Ile Thr Thr Leu
        50                  55                  60

Pro Ala Leu Pro Glu Asp Gly Gly Ser Gly Ala Phe Pro Pro Gly His
65                  70                  75                  80

Phe Lys Asp Pro Lys Arg Leu Tyr
                85

<210> SEQ ID NO 4
<211> LENGTH: 630
<212> TYPE: DNA
<213> ORGANISM: Human

<400> SEQUENCE: 4
ctgggggacc gcgggcgcgg ccgcgcgctg ccgggcggga ggctgggggg ccggggccgg      60
ggccgtgccc cggagcgggt cggaggccgg ggccggggcc gggggacggc ggctccccgc     120
gcggctccag cggctcgggg atcccggccg ggccccgcag ggaccgctgc agccgggagc     180
atcaccacgt tgcccgcctt gcccgaggat ggcggcagcg gcgccttccc gcccggccac     240
ttcaaggacc ccaagcggct gtactgcaaa acgggggct tcttcctgcg catccacccc      300
gacggccgag ttgacggggt ccgggagaag agcgacccctc acatcaagct acaacttcaa    360
gcagaagaga gaggagttgt gtctatcaaa ggagtgtgtg ctaaccgtta cctggctatg     420
aaggaagatg gaagattact ggcttctaaa tgtgttacgg atgagtgttt ctttttgaa      480 cgattggaat ctaataacta caatacttac cggtcaagga aatacaccag ttggtatgtg     540
gcactgaaac gaactgggca gtataaactt ggatccaaaa caggacctgg gcagaaagct     600
atactttttc ttccaatgtc tgctaagagc                                      630

<210> SEQ ID NO 5
<211> LENGTH: 258
<212> TYPE: DNA
<213> ORGANISM: Human

<400> SEQUENCE: 5

-continued

```
ctgggggacc gcgggcgcgg ccgcgcgctg ccgggcggga ggctgggggg ccggggccgg      60
ggccgtgccc cggagcgggt cggaggccgg ggccggggcc gggggacggc ggctccccgc     120
gcggctccag cggctcgggg atcccggccg ggccccgcag ggaccgctgc agccgggagc     180
atcaccacgc tgcccgcctt gcccgaggat ggcggcagcg gcgccttccc gcccggccac     240
ttcaaggacc ccaagcgg                                                   258

<210> SEQ ID NO 6
<211> LENGTH: 264
<212> TYPE: DNA
<213> ORGANISM: Human

<400> SEQUENCE: 6
ctgggggacc gcgggcgcgg ccgcgcgctg ccgggcggga ggctgggggg ccggggccgg      60
ggccgtgccc cggagcgggt cggaggccgg ggccggggcc gggggacggc ggctccccgc     120
gcggctccag cggctcgggg atcccggccg ggccccgcag ggaccgctgc agccgggagc     180
atcaccacgc tgcccgcctt gcccgaggat ggcggcagcg gcgccttccc gcccggccac     240
ttcaaggacc ccaagcggct gtac                                            264
```

TRUNCATED 24KDA BASIC FIBROBLAST GROWTH FACTOR

This application claims priority to U.S. provisional application No. 60/370,212, filed Apr. 8, 2002, entitled "Truncated 24 kDa Basic Fibroblast Growth Factor (24 kDa FGF-2) Which Inhibits Cell Migration" which is hereby incorporated by reference in its entirety.

This invention was funded in part by grants and contracts from the National Heart, Lung, and Blood Institute, National Institutes of Health, which provides to the United States government certain rights in this invention.

This invention was made with government support under Contract No. CA81209 by the National Institutes of Health. The U.S. Government has certain rights to this invention.

BACKGROUND OF THE INVENTION

Throughout this application various publications are referenced, many referenced by numbers in parenthesis. Full citations for these publications are provided at the end of the Detailed Description of the Invention. The disclosure of these publications are hereby incorporated by reference, in their entirety, in this application.

The invention is in the field of biochemistry and medicine relates to the 24,000 Dalton form of fibroblast growth factor-2 (24 kDa FGF-2). Specifically, this invention relates to any and all portions of the 24 kDa FGF-2 that inhibit the migration of eukaryotic cells but lack the growth promoting activity associated with full length 24 kDa FGF-2.

Figure 1:
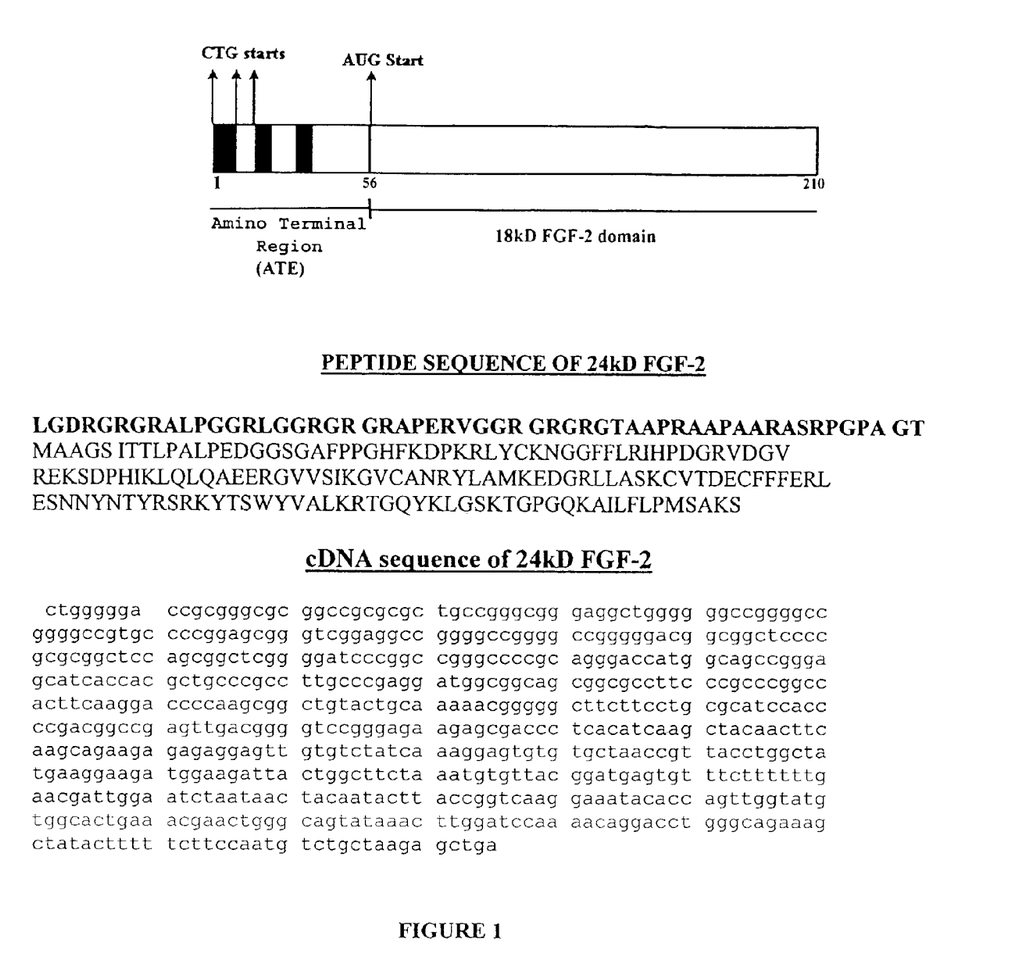
FIG. 1 shows a schematic diagram of 24 kDa FGF-2, the peptide sequence of 24 kDa FGF-2 (SEQ ID NO: 1), and the nucleotide sequence of 24 kDa FGF-2 (SEQ ID NO: 4).

Polypeptide growth factors stimulate the growth and migration of a variety of cells (1). One of these polypeptide growth factors that promotes endothelial cell growth, migration, and invasion is basic fibroblast growth factor (FGF-2) (2-5). FGF-2 is part of a large family of fibroblast growth factors consisting of at least 9 separate gene products, which share a common domain. The single copy gene for FGF-2 encodes for multiple forms of the protein of 24, 22.5, 22, and 18 kDa with the three higher molecular weight FGF-2s ("hmwFGF-2") produced by initiation of translation at CUG initiation sites upstream from the AUG codon (FIG. 1) (6;7). The 24 kDa FGF-2 form is comprised of the 18 kDa FGF-2 with an additional 55 amino acids on the amino terminal end. The structure of the mRNA indicates that its synthesis is translationally controlled. The cellular localization and apparent functions of 18 kDa and hmwFGF-2 differ. The 18 kDa FGF-2 is mostly cytoplasmic and is exported to the cell surface where it is localized to the basement membrane or extracellular matrix in association with matrix heparins and heparans (8;9). In contrast, undetectable or extremely low levels of hmw FGF-2 are present in the media of the cultured cells studied to date. Instead, the majority of the cellular hmwFGF-2 is directly translocated into the nucleus (10;11). The residues associated with nuclear translocation are RG repeats found at several sites within the amino terminal region of hmwFGF-2 (12). Thus, 18 kDa FGF-2 has been considered to be an external regulator of endothelial cell behaviour while the hmwFGF-2 is thought to generate intranuclear autocrine signals.

We demonstrated that exogenously applied recombinant 24 kDa FGF-2 could regulate cell behavior in two ways, stimulation of cell proliferation and inhibition of migration (13). The increase in proliferation was comparable to that promoted by 18 kDa FGF-2 indicating that the stimulation was independent of the additional amino terminal peptide. On the other hand, the effect on migration was opposite to that of 18 kDa FGF-2. While 18 kDa FGF-2 promoted cell motility, 24 kDa FGF-2 inhibited migration of endothelial cells by 50% and mammary carcinoma MCF-7 cells by greater than 70%, even in the presence of unrelated mitogens that promote cell migration such as vascular endothelial growth factor (VEGF) and insulin like growth factor-1 (IGF-1). Using antibodies specific to the amino terminal end (amino terminal 55 amino acids, "ATE") or antibodies to the 18 kDa regions of the 24 kDa FGF-2, we localized the inhibition of migration to the ATE and stimulation of growth to the 18 kDa domain of 24 kDa FGF-2. Thus, it was concluded that 24 kDa FGF-2 affects cell behaviour differently than 18 kDa FGF-2 and that the ATE region, which is absent from the 18 kDa FGF-2, is responsible for this difference.

The present invention is a truncated form of Fibroblast Growth Factor, thus it has never before been described as an independent molecule. The full length Fibroblast Growth Factor has both an inhibitory activity and a proliferative activity, i.e., it stimulates cells to grow which is an unwanted activity in cancer therapy. Growth factors are considered pro-migratory and pro-angiogenic, and they can be used to stimulate angiogenesis in patients with vascular insufficiencies. The unexpected result of the present invention includes the separation of the inhibitory activity from the unwanted proliferative activity, thus allowing the use of a truncated growth factor as anti-angiogenic or an anti-migration compound. The present invention is not an anti-angiogenic alone, but it is effective against tumor cells. Thus, tumors that are not susceptible to anti-angiogenic treatment will be responsive to the present invention.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention provides methods and compositions for treating diseases and processes mediated by undesired and uncontrolled cell invasion and/or angiogenesis by administration to a subject a composition comprising an oligopeptide, chemical derivative or peptidomimetic in dosage sufficient to inhibit the invasion and/or angiogenesis. The present invention is particularly useful for treating or for suppressing the growth of tumors, the development of blood vessels resulting in retinopathy or any other diseases dependent of blood vessel formation. Administration of the composition to a human or subject with prevascularized metastasised tumors will prevent the growth or expansion of these tumors.

Figure 8A:
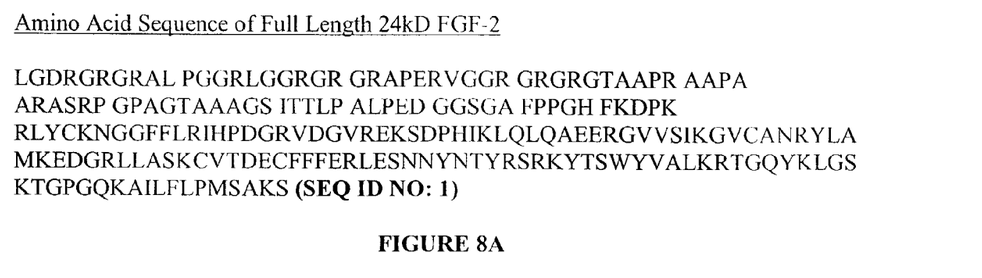
Figure 8B:
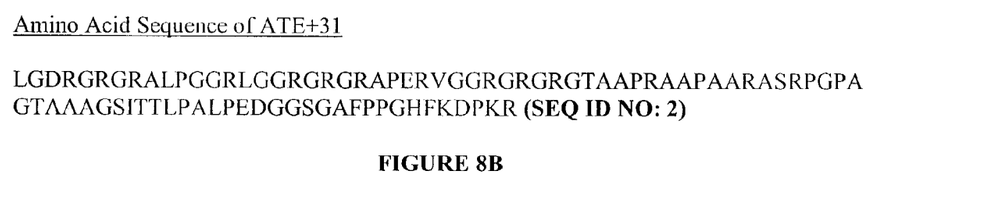
Figure 8C:
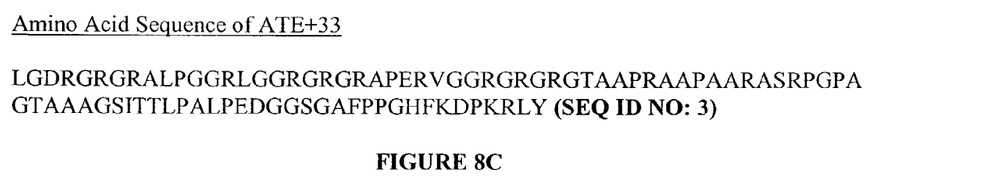
Figure 10:
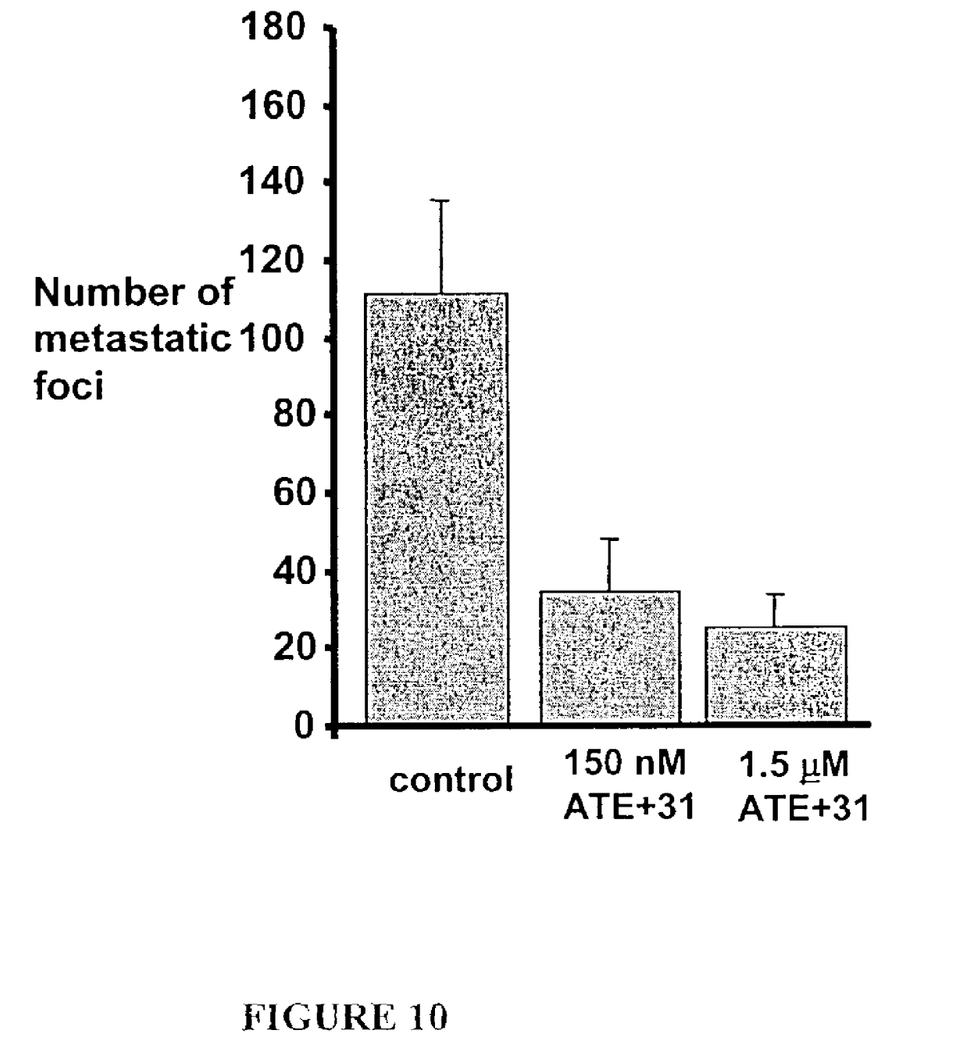
FIG. 10 shows in vivo assessment of the effect of ATE+31 on metastasis. Administration of ATE+31 inhibits the formation of metastatic foci in the lungs of mice. MDA MB231 cells (200,000) were injected into the tail vein of SCID mice and ATE+31 administered by intravenous injection twice a week for 6 weeks. Data represents the number of foci counted per mouse lung.

Thus, the present invention is directed to a novel protein containing any portion of the full length 24 kDa fibroblast growth factor, the amino acid sequence of the full length 24 kDa fibroblast growth factor is shown in FIG. 8A (SEQ ID NO: 1). The present invention is directed to any portion of the full length 24 kDa fibroblast growth factor, either continuous or non-continuous, or a substitution variant, addition variant or other chemical derivative thereof, that inhibits migration of mammalian cells in vitro and reduces or completely blocks the growth of blood vessels, tumors growth, or any physiologic or pathologic response that is dependent on cell migration in vivo. Preferably the ATE+31 truncated protein has an amino acid sequence as shown in FIG. 8B (SEQ ID NO: 2) and the ATE+33 truncated protein has an amino acid sequence as shown in FIG. 8C (SEQ ID NO: 3). For in vivo methods, it is highly preferable to administer a pharmaceutical composition (comprising the polypeptide formulated in a pharmaceutically accepted diluent, adjuvant, excipient, carrier, or the like) to the subject, in an amount effective to modulate the migration of cells and the growth of tumor and blood vessels in vivo.

The present invention is further directed to a pharmaceutical composition useful for inhibiting the growth of tumors or angiogenesis, comprising a protein, variant or chemical derivative including a peptidomimetic or an multimeric peptide and a pharmaceutically acceptable carrier or exipient.

Also provided is a method for inhibiting cell migration, invasion, migration-induced cell proliferation or angiogenesis in a subject having disease or condition associated with undesired cell migration, invasion, migration-induced proliferation, or angiogenesis comprising administering to the subject an effective amount of a pharmaceutical composition as described above.

In any of the foregoing methods, the disease or condition being treated may be primary tumor growth, tumor invasion or metastasis, atherosclerosis, post-balloon angioplasty vascular restenosis, neointima formation following vascular trauma, vascular graft restenosis, fibrosis associated with a chronic inflammatory condition, lung fibrosis, chemotherapy-induced fibrosis, wound healing with scarring and fibrosis, psoriasis, deep venous thrombosis, retinopathy or any another disease or condition in which angiogenesis is pathogenic.

An effective amount of polypeptide is defined herein as that amount of polypeptide empirically determined to be necessary to achieve a reproducible change in cell growth rate or migration, angiogenesis, or tumor size, (as determined by microscopic or macroscopic visualization and estimation of cell doubling time, or nucleic acid synthesis assays), as would be understood by one of ordinary skill in the art. An effective dose may be between about 1 ng/kg body weight and about 10 g/kg body weight, preferably between about 1 microg/kg body weight and about 100 mg/kg body weight, more preferably between about 100 microg/kg body weight and 10 mg/kg body weight.

For methods which involve the in vivo administration of polypeptides of the invention, it is contemplated that the polypeptides will be administered in any suitable manner using an appropriate pharmaceutically-acceptable vehicle, e.g., a pharmaceutically-acceptable diluent, adjuvant, excipient or carrier. Thus, the invention further includes compositions, e.g., pharmaceutical compositions, comprising one or more polypeptides of the invention. By pharmaceutical composition it is meant a composition that may be administered to a mammalian host, e.g., orally, topically, parenterally (including, but not limited to subcutaneous injections, intravenous, intramuscular, intracisternal injection or infusion techniques), by inhalation spray, or rectally, in unit dosage formulations containing conventional non-toxic carriers, diluents (including, but not limited to calcium carbonate, sodium carbonate, lactose, calcium phosphate, sodium phosphate, kaolin, water), adjuvants, vehicles, and the like, including but not limited to flavoring agents, preserving agents; granulating and disintegrating agents; binding agents; time delay materials; oils; suspending agents; dispersing or wetting agents; anti-oxidants; and emulsifiers.

The definition of polypeptides of the invention is intended to include within its scope variants thereof. The polypeptide variants contemplated include purified and isolated polypeptides having amino acid sequences that differ from the exact amino acid sequences of such polypeptides by conservative substitutions, as recognized by those of skill in the art, that are compatible with the retention of the inhibitory activity of polypeptide. The term "variants," when used to refer to polypeptides, also is intended to include polypeptides having amino acid additions, including but not limited to additions of a methionine and/or leader sequence to promote translation and/or secretion; additions of peptide sequences to facilitate purification (e.g., polyhistidine sequences and/or epitopes for antibody purification); and additions of polypeptide-encoding sequences to produce fusion proteins. The term "variants" also is intended to include polypeptides having amino acid deletions at the amino terminus, the carboxy terminus, or internal of amino acids that are non-conserved amongst mammalian sequences, and that are compatible with the retention of the inhibitory activity of the polypeptide to which the deletions have been made.

The term "variant" also is intended to include polypeptides having modifications to one or more amino acid residues that are compatible with retaining inhibitory activity of the polypeptide. Such modifications include glycosylations and the addition of other substituents (e.g., labels, compounds to increase serum half-life (e.g., polyethylene glycol), and the like.

In yet another aspect, the invention includes analogs of the polypeptides of the invention. The term "analog" refers to polypeptides having alterations involving one or more amino acid insertions, internal amino acid deletions, and/or non-conservative amino acid substitutions (replacements). The definition of analog is intended to include within its scope variants of analog polypeptides embodying such alterations. The term "mutant," when used with respect to polypeptides herein, is intended to refer generically to 24 kDa FGF-2, analogs, and variants of analogs.

The present invention also provides purified and isolated polynucleotides (i.e., nucleic acids) encoding all of the polypeptides of the invention, including but not limited to cDNAs and genomic DNAs encoding 24 kDa FGF-2 biologically active fragments thereof, and DNAs encoding the same. Distinct polynucleotides encoding any polypeptide of the invention by virtue of the degeneracy of the genetic code are within the scope of the invention. The DNA sequence of the full length 24 kDa fibroblast growth factor is shown if FIG. 9A (SEQ ID NO: 4), and the DNA sequence corresponding to amino acid sequence of the ATE+31 truncated protein of the present invention is shown in FIG. 9B (SEQ ID NO: 5), and the amino acid sequence of the ATE+33 truncated protein is shown in FIG. 9C (SEQ ID NO: 6).

Additional aspects of the invention include vectors which comprise nucleic acids of the invention; and host cells transformed or transfected with nucleic acids or vectors of the invention. Preferred vectors of the invention are expression vectors wherein nucleic acids of the invention are operatively connected to appropriate promoters and other control sequences that regulate transcription and/or subsequent translation, such that appropriate prokaryotic or eukaryotic host cells transformed or transfected with the vectors are capable of expressing the polypeptide encoded thereby.

In a related aspect of the invention, host cells such as prokaryotic and eukaryotic cells, especially unicellular host cells, are modified to express polypeptides of the invention. Host cells may be stably transformed or transfected with isolated DNAs of the invention in a manner allowing expression of polypeptides of the invention therein. Thus, the invention further includes a method of making polypeptides—of the present invention. In a preferred method, a nucleic acid or vector of the invention is expressed in a host cell, and a polypeptide of the invention is purified from the host cell or the host cell's growth medium.

BRIEF DESCRIPTION OF THE DRAWINGS

FIG. 2 shows the effect of truncated forms of 24 kDa FGF-2 on cell migration and proliferation. A. The effects of 24 kDa FGF-2, ATE+31 (the amino terminal end plus 31 amino acids), ATE+20 (amino terminal end plus 20 amino acids), and ATE (the amino terminal end only) on MCF-7 cell migration were tested in a Boyden Chamber assay. Proteins at $6.6 \times 10^{-11}$ M (open bars), $3.3 \times 10^{-10}$ M (filled bars), or $8 \times 10^{-10}$ M (hatched bars) were employed and the cell migration rates in response to 10 ng/ml IGF-1 were measured. Results are presented as a percent of the migration rate of MCF-7 cells in the presence of 10 ng/ml IGF-1 alone. B. Proliferation of MCF-7 cells by ATE+31. Cells were treated with 18 kDa FGF-2, 24 kDa FGF-2, or ATE+31 at $4 \times 10^{-10}$ M and the effect on the rate of thymidine incorporation determined. Both 18 kDa FGF-2 and 24 kDa FGF-2 stimulated thymidine incorporation 8 to 10 fold while ATE+31 had no effect. Results are presented relative to the rate of thymidine incorporation in the absence of any growth factor.

FIG. 6 shows the in vivo assessment of the effect of ATE+31 on angiogenesis. 6A. Female athymic Ncr nude mice were injected subcutaneously at three sites near the abdominal midline with matrigel (500~L) mixed with heparin (25 .Ilg), FGF-2 (20 nM) and ATE+31 as indicated. Injection sites were chosen such that each animal received a positive control plug (FGF-2 and heparin), a negative control plug (heparin plus buffer) and a plug containing the treatment to be tested (FGF-2, heparin and ATE+31). All treatments were tested in triplicate. 6B. Quantitative analysis of neovascular development in matrigel plugs in vivo. Matrigel plugs were excised from the animals, dispersed in water and incubated at 37° C. overnight. Hemoglobin levels were determined using Drabkin's solution (Sigma) according to the manufacturers' instructions. The results were quantitated spectrophotometrically at 540 nm and are presented as a function of the amount of hemoglobin present in plugs not containing added growth factor (left panel). The basal level of angiogenesis occurring in the absence of 18 kDa FGF-2 was subtracted from the hemoglobin levels in the treated plugs and the results presented as a percentage of that occurring in the presence of 18 kDa FGF-2 alone (100%, right panel).

FIG. 8 shows the amino acid sequence of 8A. the full length 24 kDa fibroblast growth factor, 8B. the amino acid sequence of the ATE+31 truncated fibroblast growth factor, and 8C. the amino acid sequence of the ATE+33 truncated fibroblast growth factor.

FIG. 9 shows the nucleic acid sequence of 9A. the full length 24 kDa fibroblast growth factor, 9B. the nucleic acid sequence of the ATE+31 truncated fibroblast growth factor, and 9C. the nucleic acid sequence of the ATE+33 truncated fibroblast growth factor.

DETAILED DESCRIPTION OF THE INVENTION

The present inventor and his colleagues previously determined that the 24 kDa, 22.5 kDa, and 22 kDa FGF-2 form of basic fibroblast growth factor inhibit the migration of cells in culture.

The present inventor has now identified truncated forms of 24 kDa FGF-2 which act as inhibitors of tumor growth, angiogenesis, and invasiveness. The proteins are potent and specific inhibitors of (a) cell invasion, (b) angiogenesis at tumor sites including sites of metastasis, (c) blood vessel formation leading to other pathologies such as but not limited to retinopathy.

In Vitro Testing of Compositions

Migration and Growth Assays: For migration assays, MCF-7 cells or endolithial cells were harvested with trypsin, counted, centrifuged, and resuspended at 1×10$^5$ cells in 0.5 ml Dulbecco's modified Eagle's medium/0.5% bovine serum albumin. Cells were added to the upper well of a Boyden chamber containing an 8.0-μm pore size polycarbonate membrane separating the two chambers of a 6.5-mm Transwell (Costar). The upper wells were placed into the lower chamber containing 0.75 ml of Dulbecco's modified Eagle's medium/ 0.5% bovine serum albumin to which 10 ng/ml of IGF-2 (Sigma) or 10 ng/ml VEGF (Sigma) was added as a chemoattractant. Both chambers contained 24 kDa FGF-2 or truncated forms at the appropriate concentrations. After 4-6 hrs incubation at 37° C. in 5% CO2, non-migratory cells on the upper membrane surface were removed with a cotton swab and the cells which traversed and spread on the lower surface of the filter were fixed and stained with Diff-Quik (Dade-Behring). The filter was mounted on a glass slide, and 4 phase-contrast photomicrographs/membrane were taken at a magnification of 100×. The number of cells per field was counted from contact sheets and the result compared with control chamber with had no 24 kDa FGF-2 added.

To measure growth rates, MCF-7 cells (6×10$^3$) were plated in growth medium for 48 hrs, the medium changed to assay medium containing henol red-free modified Eagle's medium supplemented with 1 mM sodium pyruvate and 0.3% lactalbumin hydrolysate plus or minus growth factors, and the cultures were allowed to incubate an additional 24 hrs. Two hrs prior to the termination of the experiment $^3$H-thymidine was added. The cultures were washed with PBS and then ice cold methanol (2×), 5% trichloracetic acid was added two times for 10 min each, and the DNA extracted with 0.3 N NaOH. The number of cpm incorporated was determined by liquid scintillation.

In Vivo Study of Trucated Forms of 24 FGF-2

In Vivo Assessment of Angiogenesis Using the Matrigel Plug Assay: Ice-cold matrigel (500 μL) (Collaborative Biomedical Products, Inc., Bedford, Mass.) was mixed with heparin (50 μg/ml), FGF-2 (400 ng/ml) and ATE+31 as indicated. The matrigel mixture was injected subcutaneously into 4-8 week-old female athymic Ncr nude mice at sites near the abdominal midline, 3 injections per mouse. Injection sites were chosen such that each animal received a positive control plug (FGF-2 and heparin), a negative control plug (heparin plus buffer) and a plug containing the treatment to be tested (FGF-2, heparin and ATE+31). All treatments were tested in triplicate. Animals were sacrificed by cervical dislocation 5 days post injection. The mouse skin was detached along the abdominal midline and the matrigel plugs recovered and scanned immediately at high resolution. Plugs were then dispersed in water and incubated at 37° C. overnight. Hemoglobin levels were determined using Drabkin's solution (Sigma).

In Vivo Assessment of the Effect of ATE+31 on Tumor Growth. Two million MatLyLu prostate carcinoma cells were implanted into 0.5 ml of matrigel in the presence or absence of 400 nM ATE+31 and the gels placed subcutaneously into 4-8 week-old female athymic Ncr nude mice at sites near the abdominal midline. After 7 days the gels were removed, photographed and weighed. Each animal was injected with Matrigel containing no cells or protein, with cells alone, and with cells and protein and the relative weight of each compared within the same animal.

Therapeutic Compositions and Methods

The preferred animal subject of the present invention is a mammal. The invention is particularly useful in the treatment of human subjects. By the term "treating" it is intended the administering to subjects of a pharmaceutical composition comprising any of the truncated forms of 24 kDa FGF-2 that have inhibitory activity toward cell migration leading to inhibition of tumor development and angiogenesis.

The pharmaceutical compositions of the present invention wherein the truncated form(s) of is combined with pharmaceutically acceptable excipient or carrier, may be administered by any means that achieve their intended purpose. Amounts and regimens for the administration can be determined readily by those with ordinary skill in the clinical art of treating any of the particular diseases. Preferred amounts are described below.

Administration may be by parenteral, subcutaneous (sc), intravenous (iv), intramuscular, intraperitoneal, transdermal, topical or inhalation routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the truncated 24 kDa FGF-2 protein is contained in an amount effective to achieve its intended purpose. While individual needs vary, determination of optimal ranges of effective amounts of each component is within the skill of the art. Typical dosages comprise 0.1 to 100 mg/kg body weight, though more preferred dosages are described for certain particular uses, below.

As stated above, in addition to the pharmacologically active protein, the new pharmaceutical preparations may contain suitable pharmaceutically acceptable carriers comprising excipients and auxiliaries which facilitate processing of the active compounds into preparations which can be used pharmaceutically as is well known in the art. Suitable solutions for administration by injection or orally, may contain from about 0.01 to 99 percent, active compound(s) together with the excipient.

The pharmaceutical preparations of the present invention are manufactured in a manner which is itself known, for example, by means of conventional mixing, granulating, dissolving, or lyophilizing processes. Suitable excipients may include fillers binders, disintegrating agents, auxiliaries and stabilizers, all of which are known in the art. Suitable formulations for parenteral administration include aqueous solutions of the proteins in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension.

The pharmaceutical formulation for systemic administration according to the invention may be formulated for enteral, parenteral or topical administration, and all three types of formulation may be used simultaneously to achieve systemic administration of the active ingredient.

For topical application, the proteins of the present invention may be incorporated into topically applied vehicles such as salves or ointments, which have both a soothing effect on the skin as well as a means for administering the active ingredient directly to the affected area.

The carrier for the active ingredient may be either in sprayable or nonsprayable form. Non-sprayable forms can be semisolid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Examples of preferred vehicles for non-sprayable topical preparations include ointment bases, e.g., polyethylene glycol-1000 (PEG-1000); conventional creams such as HEB cream; gels; as well as petroleum jelly and the like.

Other pharmaceutically acceptable carriers for truncated form(s) of 24 kDa FGF-2 protein according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension.

Having now generally described the invention, the same will be more readily understood through reference to the following examples which are provided by way of illustration, and are not intended to be limiting of the present invention.

EXAMPLE I

Figure 2:
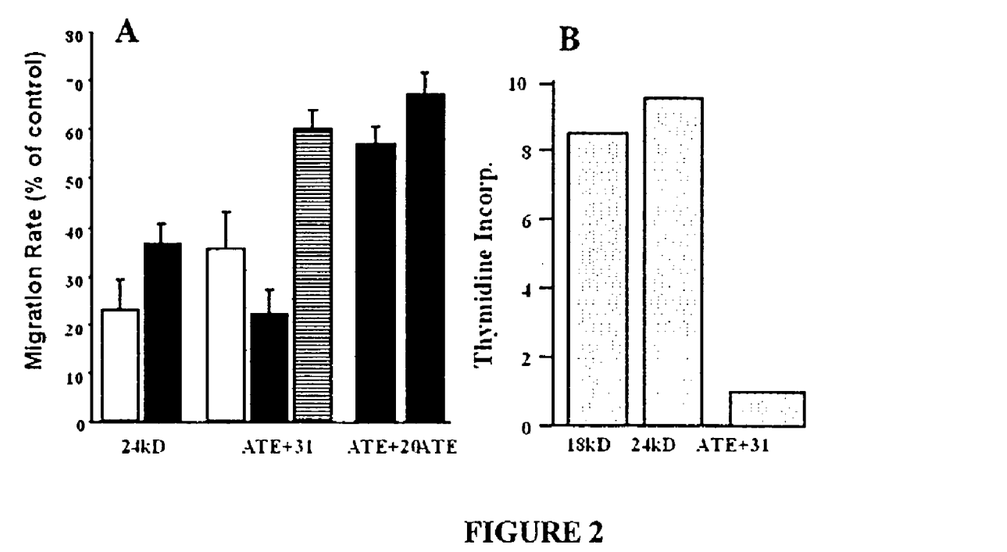

Truncated forms of 24 kDa FGF-2 were generated by deletion mutagenesis through the placement of stop codons within the 24 kDa FGF-2 cDNA. To determine the effect of these truncations on the growth promoting activity of 24 kDa FGF-2, peptides were added to MCF-7 cells and the rate of cell proliferation, as determined by thymidine incorporation, compared to 24 kDa and 18 kDa FGF-2 (FIG. 2). 24 kDa FGF-2 stimulated proliferation equally as well as 18 kDa FGF-2 (8-10-fold). However, no stimulation of proliferation was observed with either of the truncated forms of 24 kDa FGF-2 at concentrations equal to those used for 24 or 18 kDa FGF-2 (FIG. 2). Increasing the concentration of ATE+31 to $1\times10^{-9}$ did not promote proliferation. Thus, the growth stimulatory effect of 24 kDa FGF-2 is dependent on the carboxy terminal portion of 24 kDa FGF-2. However, this was not the case with the inhibition of migration. Employing the Boyden chamber assays and IGF-1 as a chemoattractant, we observed a decrease in MCF-7 cell migration to 35.5±8% of control in the presence of $6.6\times10^{-11}$ M ATE+33 and to 22.3±5% with $3.3\times10^{-10}$ M ATE+31. The decline in motility with $3.3\times10^{-10}$ M ATE+31 was equal to the maximal effect observed with full length 24 kDa FGF-2 (22.1±6%), although the truncated protein required 5 times the concentration of the larger molecule. In both cases, increasing the concentration of the proteins by another 5-fold resulted in a reduction in inhibitory activity. At $3.3\times10^{-10}$ M, 24 kDa FGF-2 was less effective at inhibiting migration while at $8\times10^{-10}$ M ATE+31 only inhibited migration to 61±4% of control. Deletion of additional portions of 24 kDa FGF-2 reduced the inhibitory activity. ATE+20 could only reduce migration to 58% at $3.3\times10^{-10}$ M. Removal of additional amino acids had no further effect. Endothelial cell migration using VEGF as a chemoattractant was similarly affected with $3.3\times10^{-10}$ M ATE+31 reducing mobility to 24% (data not shown). These results demonstrate that the inhibition of migration activity of 24 kDa FGF-2 is localized to the amino terminal end and does not require either the published receptor binding sites nor the heparin binding sites found within 18 kDa FGF-2.

EXAMPLE II

Figure 3:
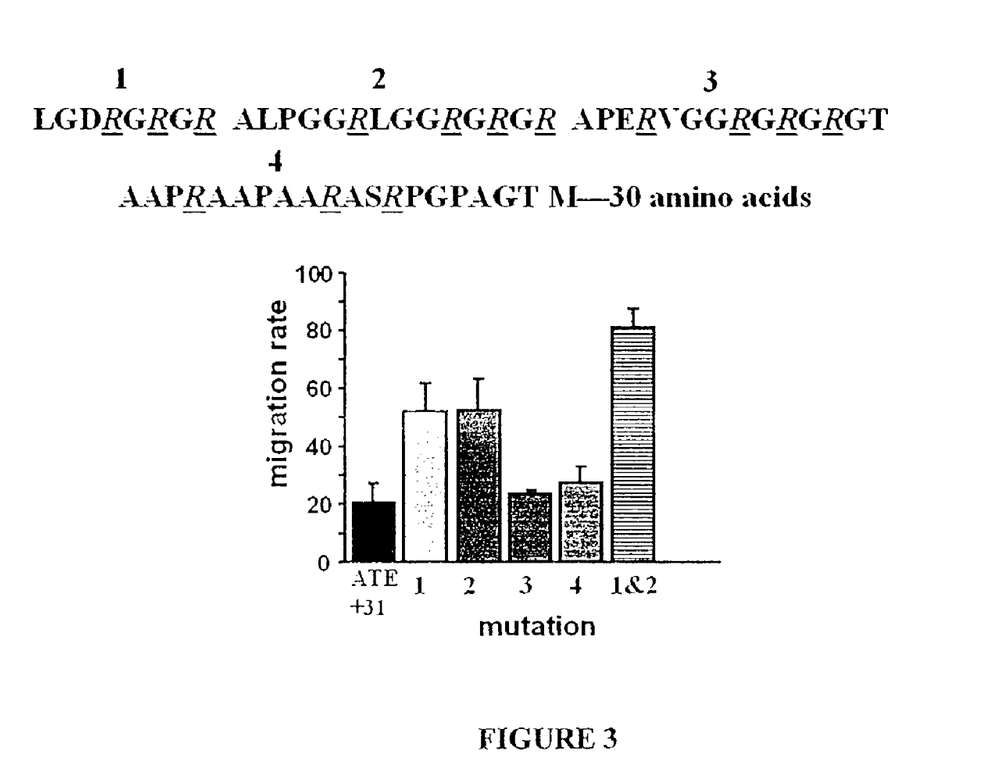
FIG. 3 shows the effect of the arginine to alanine substitution within the amino terminal region of ATE+31 (SEQ ID NO: 2) on the inhibition of migration. The amino terminal 55 amino acids of ATE+31 (SEQ ID NO: 2) was divided into 4 sub-regions and the arginines in each region were converted to alanine by site directed mutagenesis (upper panel). Each mutated protein was tested for inhibitory activity using MCF-7 cells and 10 ng/ml IGF-1 and the results presented as a percent of the migration rate in the presence of IGF-1 alone. The numbers on the x-axis refer to the regions of the amino terminal peptide in which the substitutions were made. The results show that the inhibitory activity can be localized to regions 1 and 2.

Further attempts to determine if the inhibitory activity was dependent on specific regions within the ATE involved arginine to alanine substitution. Because of the large number of arginines in the ATE, the sequence was separated into 4 regions each containing 3 or 4 arginines (FIG. 3). Each region was modified separately and the effect on inhibition of migration was tested and compared to the unmodified ATE+31. Conversion of arginine to alanine in the two regions at the carboxy terminal end of the ATE (3 and 4) had little effect on the migration rates; these molecules still inhibited migration by 70 to 75%. However, arginine to alanine substitutions within either of the two regions at the amino terminal end (1 and 2) reduced the inhibitory activity of ATE+31; cell migration was 50% of untreated cultures as opposed to 20% for the wild type ATE+31. The inhibition of migration could be reduced even further by combining regions 1 and 2 resulting in less than 15% inhibition of migration.

EXAMPLE III

Figure 4:
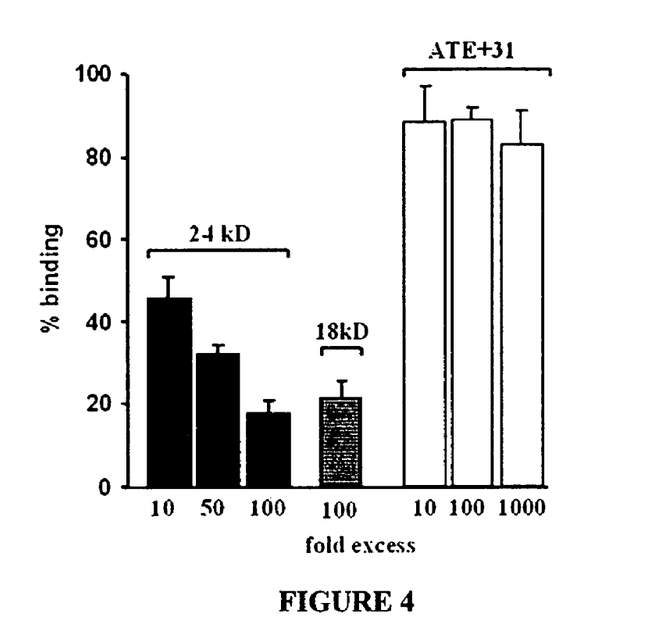
FIG. 4 shows ATE+31 does not compete with 24 kDa FGF-2 for binding to FGFR1. 3T3 cells were incubated at 4° C. for 2 hr with 2 ng $^{125}$I-24 kDa FGF-2 and increasing concentrations of unlabeled 24 kDa FGF-2 or ATE+31. Values shown are the means of triplicate samples±S.D. and are representative of three or more experiments. The results are presented as a percent of maximal 24 kDa FGF-2 binding in the absence of competitor.
Figure 5:
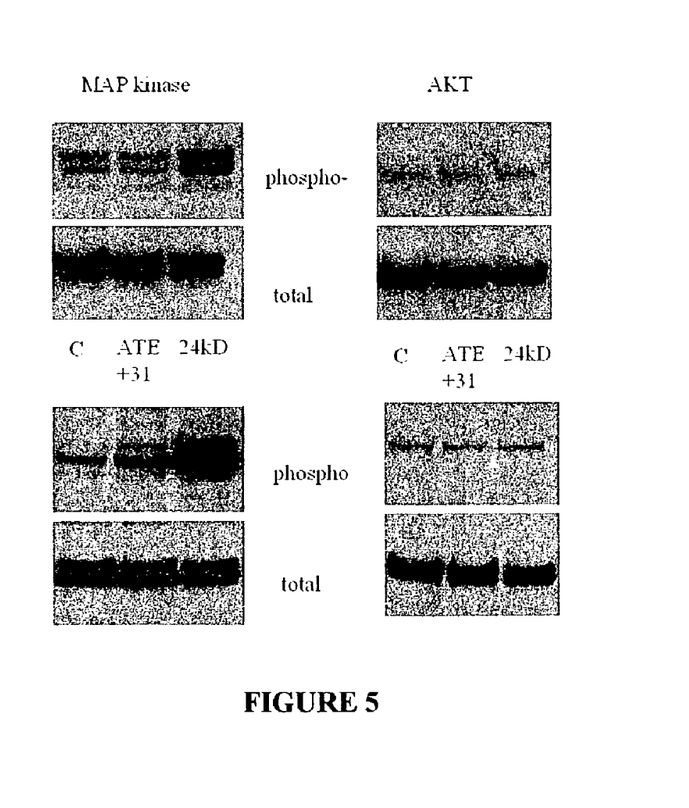
FIG. 5 shows failure of ATE+31 to stimulate ERK phosphorylation. MCF-7 and endothelial cells were treated with 1 ng/ml of 24 kDa FGF-2 or 0.37 ng/ml ATE+31 for 10 min, the cells were extracted, and the protein lysates immunoblotted with antibodies to either phospho-ERK (pERK) or total ERK.

The localization of the inhibitory activity to the amino terminal end of 24 kDa FGF-2 suggests that there is some, interaction between this portion of the protein and the cells it is affecting. In previous studies, it was shown that the FGF receptor to which 24 kDa FGF-2 binds in endothelial, MCF-7, and 3T3 cells is FGFR1. To determine whether ATE+31 contains a major binding domain for interaction with FGFR1, competition binding experiments were performed with iodinated 24 kDa FGF-2 vs. unlabeled 24 kDa FGF-2, 18 kDa FGF-2, or ATE+31 (FIG. 4). Competition between labeled 24 kDa FGF-2 and itself resulted in a dose dependent decline in the binding of labeled protein with an 81±3% decrease in binding at a 100-fold excess. At this concentration, 18 kDa FGF-2 also caused a similar reduction in the binding of the 24 kDa FGF-2 (79±5%). However, ATE+31 had no significant effect on the binding of $^{125}$I-24 kDa FGF-2, even at a 1000-fold excess, suggesting that no major FGFR1 binding sites are found within the amino terminal portion of 24 kDa FGF-2. To determine if ATE+31 had the ability to activate an FGFR1 regulated signalling pathway, its effect on ERK1/2 activation was analysed using phospho-specific antibodies (FIG. 5). In both MCF-7 cells and endothelial cells, 24 kDa FGF-2, at a concentration of $4\times10^{-11}$ M, stimulated the phosphorylation of ERK 1/2, a response which also occurs in 3T3 cells. However, at the same molar concentration, ATE+31 failed to affect ERK1/2 phosphorylation in these cells. Increasing the concentration to $4\times10^{-10}$ M had no effect on the level of ERK phosphorylation.

EXAMPLE IV

Figure 6A:
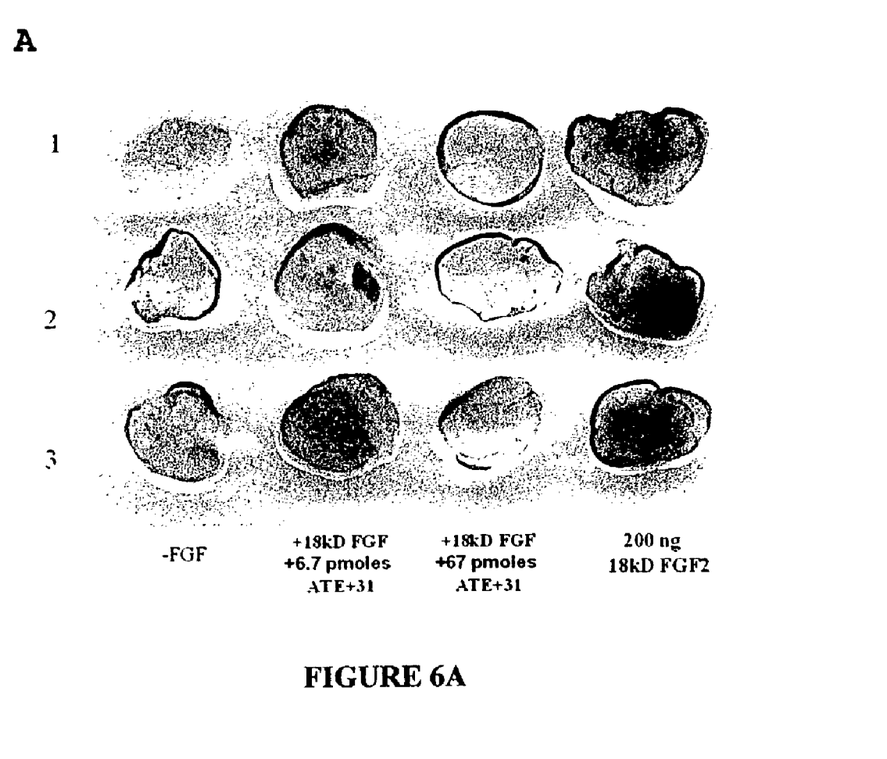
Figure 6B:
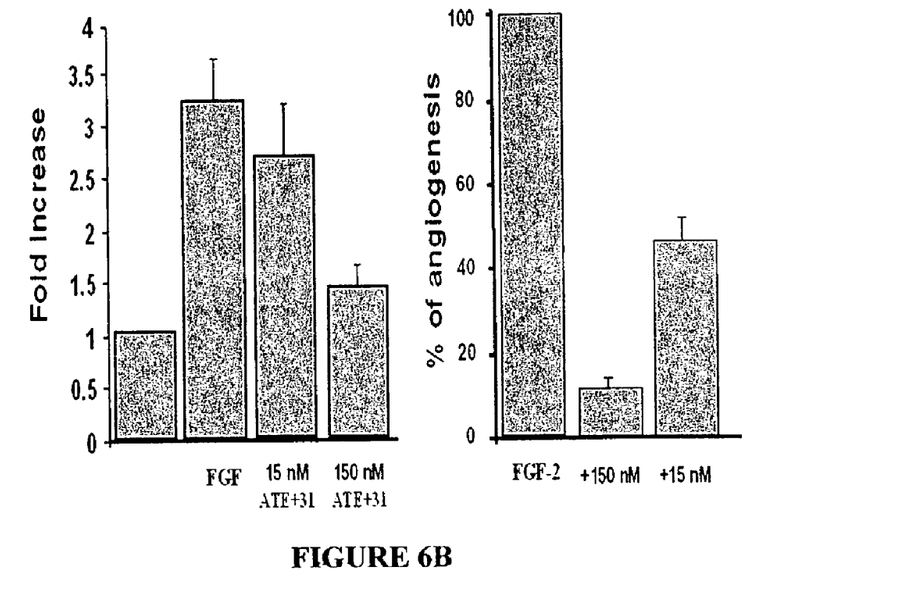

The effect of ATE+31 on angiogenesis was tested directly by implanting matrigel plugs infused with vehicle, $4\times10^{-11}$ M 18 kDa FGF-2, and 18 kDa FGF-2 plus 15 or 150 nM ATE+31 into mice and measuring the degree of vascular formation. In the presence of FGF-2 alone, there was a robust angiogenic response as indicated by the pink hue distributed throughout the plug (FIG. 6). In the presence of 15 nM ATE+31, the amount of vascular development was reduced in all three mice while at 150 nM the amount of vascularization was indistinguishable from the plugs containing no 18 kDa FGF-2 (FIG. 6*a*). To obtain a more quantitative analysis of the effects of ATE+31 on angiogenesis, the hemoglobin content within each plug was measured. In the presence of 18 kDa FGF-2 alone, the amount of hemoglobin increased 3.2-fold over the control plugs containing no added growth factor (FIG. 6*b*). The addition of 15 nM ATE+31 reduced this increase to 2.6 times control values while in the presence of 150 nM ATE+31 the increase was only 1.5 times control values. Thus, the net increase in vascular development with the higher concentration of ATE+31 was only 22% of that in plugs containing 18 kDa FGF-2 alone.

EXAMPLE V

Figure 7A:
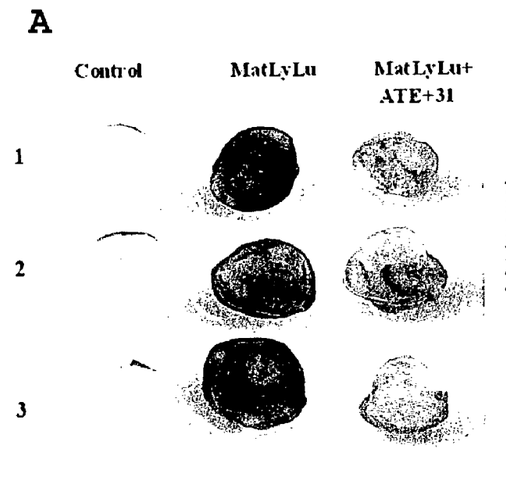
FIG. 7 shows in vivo assessment of the effect of ATE+31 on tumor growth. Two million MatLyLu prostate carcinoma cells were implanted into 0.5 ml of matrigel in the presence or absence of 400 nM ATE+31 and the gels placed subcutaneously into 4-8 week-old female athymic Ncr nude mice at sites near the abdominal midline. After 7 days the gels were removed, photographed (panel A) and weighed (B) Each animal was injected with Matrigel containing no cells or protein, with cells alone, and with cells and protein and the relative weight of each compared within the same animal.
Figure 7B:
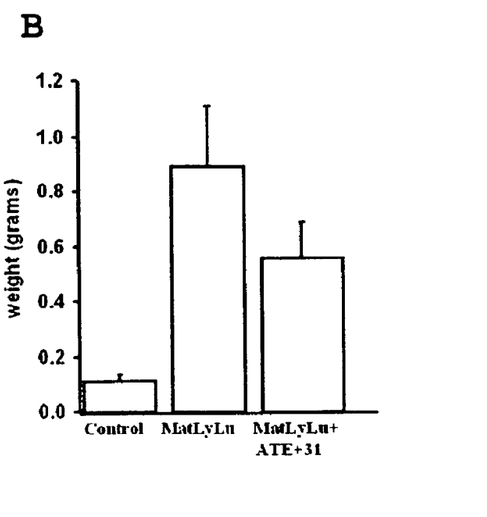

The effect of the protein on the growth of tumors was studied using matrigel plugs impregnated with 2 million MatLyLu rat prostate tumor cells in the presence or absence of 400 nM ATE+31. Plugs were implanted and ATE+31 added to the plug which remained in the animal for 7 days, removed, and then weighed. In FIG. 7A, the matrigel plugs removed from three different mice show a significant reduction in vascularization in the ATE+31-treated animals (as indicated by the red color). The average weight of the plugs is presented in FIG. 7B. The weight of untreated MatLyLu-matrigel was 0.90±0.22 grams versus 0.56±0.19 grams for the ATE+31 treated plugs. If the average starting weight of the Matrigel plugs (no cells or A TE+31) is subtracted from these values, the net reduction in tumor size in the presence of ATE+31 is 40±18%.

EXAMPLE VI

Figure 11:
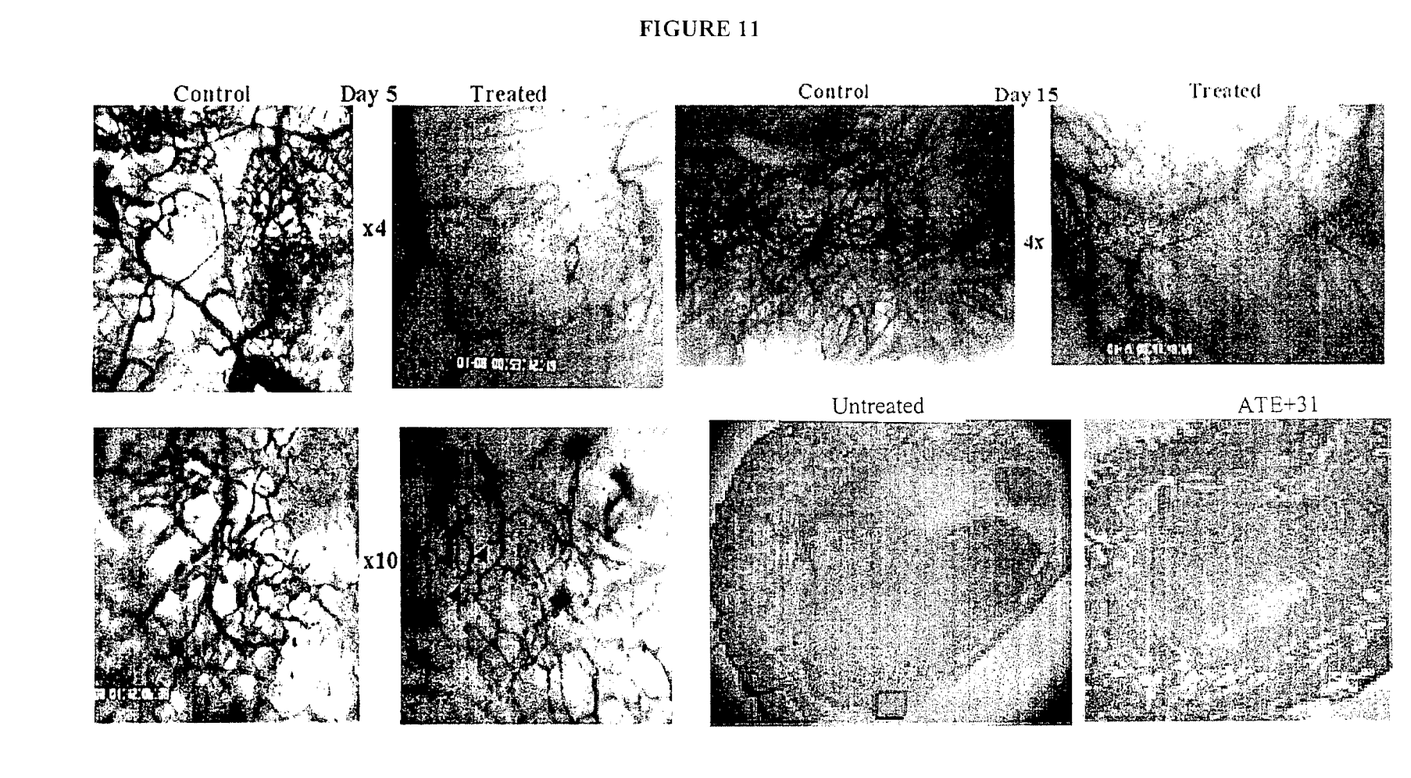
FIG. 11 shows effect of ATE+31 on MCF-7 tumors. Spheroids containing MCF-7 cells were placed within dorsal skinfold chambers and locally (superfused) treated with 20 ng of ATE+31 every two days. Left Panels, five days: Treated spheroids have a significantly less vascular supply and are fragmented. Right panels, fifteen days, upper: Vascular plexus is dense in untreated and minimal in treated. Lower: Histological evaluation of MCR-7 tumors after 15 days of ATE+31 treatment. Tissue containing the tumor was removed, fixed, sectioned, and stained with hematoxylin and eosin.

The skinfold chamber model was used to test the effect of ATE+31 on the angiogenic response to tumor development in vivo (FIG. 11). This technique allows for the continuous measurement of the changes in both rumor size and vascular density within a single animal over a prolonged period of time. Tumor spheroids with similar diameters (600-1,000 µm) formed with MCF-7 cells implanted into skinfold chambers and twenty-four hours and every two days after, 20 µl of a 1 µg/ml solution of ATE+31 (20 ng) was added directly to the spheroid. At day 5, there was already a significant difference in the density of the neovasculature within the area of the spheroid, the untreated are showed an extensive network of blood vessels in contrast to the limited response in the treated animals. In addition to the difference in the vascular density, the integrity of the growing vessels was also affected by the presence of the peptide. Higher magnification shows that the treated area contains fragment vessels (arrows). Video analysis of blood flow through these vessels revealed a diminished rate of flow, an effect we attribute to the formation of poorly differentiated blood vessels. These differences were further magnified by day 15. By day 15, the vascular plexus in the untreated animals is extremely dense, filling up most of the space within the spheroid while the treated animals have very few vessels in that area at all. Histological evaluation of the skin at day 15 shows the extent of the suppression of tumor growth by ATE+31. Comparison of the tumors indicated by dark blue area shows a dramatic difference in size. The average size of the treated tumor spheroids was only 7.8% of the untreated (1.3 mm$^2$ vs. 16.8 mm$^2$; n=3) after 15 days.

EXAMPLE VII

Figure 12:
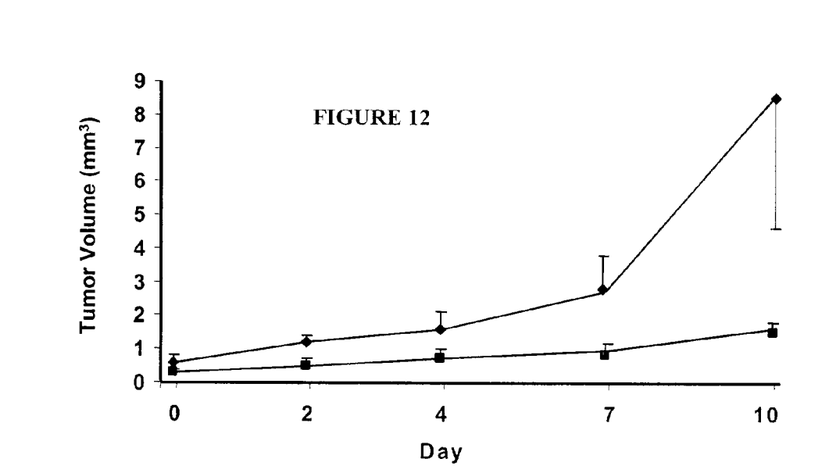
FIG. 12 shows the effect of ATE+31 on Lewis Lung Carcinoma Cells (LLC). Figures A, B, and C show comparison of the fluoroscopy labelled LLC tumors 48 hours after implantation. Before the invading blood vessels have infiltrated the tumor, the distribution of the fluorescently labelled cells was recorded and the area quantified. A. At implantation, B. untreated control, and C. treated with ATE+31 (100 ng/ml). The graph shows relative areas of tumors (n=3).

In addition to the experiments with the mammary tumor cells, we have tested the peptide against Lewis Lung Cancinoma (LLC) cells. The purpose of these experiments was to determine whether ATE+31 would be effective against a fast growing, more aggressive tumor cell (FIG. 12). Over the first 7 days, untreated tumor spheroid (♦) grew by 9-fold while the treated spheroids (■) increased by 3 times. The next three days saw a significant increase in the rate of tumor expansion in untreated animals with a final volume 28 times larger than that of the original spheroid. In contrast, ATE+31 suppressed rumor growth and the treated tumor volume was only 19% of the control. This was reflected in the vascularization of the tumor. At 6 days after implantation, a dense network was seen in untreated animals while the area containing angiogenic blood vessels in ATE+31 treated animals was small, diffuse, and poorly developed.

Determining whether ATE+31 can suppress the growth of tumors independently of its inhibition of angiogenesis was made possible by the rapid rate of LLC cell growth. This allows for a measurable increase in spheroid size prior to the infiltration of angiogenic blood vessels into the tumor itself (which occurs about 2-3 days after implantation. FIG. 12 shows that spheroids containing fluorescent-labeled cells appear as an intensely fluorescent body with distinct edges and an average area of 6.9±0.5 mm$^2$ (FIG. 12A). After 48 hour, the spheroid in control animals has spread making a larger and very diffuse structure with no inner core of the spheroid still visible (FIG. 12B; area=19.8 mm$^2$). However, treatment with ATE+31 mitigates the expansion and the spheroid body remains intact (FIG. 12C). No significant changes in are was observed (6.1±1.6 mm$^2$). Thus, suppression of tumor growth can occur even in the absense of a vascular system indicating that ATE+31 is more than an antiangiogenic molecule.

Having now fully described this invention, it will be appreciated by those skilled in the art that the same can be performed within a wide range of equivalent parameters, concentrations, and conditions without departing from the spirit and scope of the invention and without undue experimentation.

REFERENCE LIST

1. Dickoon, R. B. and Lippman, M. E. 1995. Growth factors in breast cancer. *Endocr. Rev.* 16:559-589.
2. Slavin, J. 1995. Fibroblast growth factors: at the heart of angiogenesis. *Cell Biol. Int. Rep.* 19:431-444.
3. Moscatelli, D., Presta, M., and Rifkin, D. B. 1986. Purification of a factor from human placenta that stimulates capillary endothelial cell protease production, DNA synthesis and migration. *Proc. Natl. Acad. Sci. USA* 83:2091-2095.
4. Presta, M., Moscatelli, D., Joseph-Silverstein, J., and Ritkin, D. B. 1986. Purification from a human hepatoma cell line f a basic fibroblast growth factor-like molecule that stimulates capillary endothelial cell plasminogen activator production, DNA synthesis and migration. *Mol. Cell. Biol.* 6:4060-4066.
5. Pepper, M. S. and Meda, P. 1992. Basic FGF increases junctional communication and connexin 43 expression in microvascular endothelial cells. *J. Cell. Physiol.* 153:196-205.
6. Moscatelli, D., Joseph-Silverstein, J., Presta, M., and Rifkin, D. B. 1988. Multiple forms of an angiogenic factor: basic fibroblast growth factor. *Biochimie* 70:83-87.
7. Florkiewicz, R. Z. and Sommer, A. 1989. Human basic fibroblast growth factor gene encodes four polypeptides: Three initiate translation from non-AUG codons. *Proc. Natl. Acad. Sci. USA* 86:3978-3981.
8. Miao, H.-Q., Ishai-Michaeli, R., Atzmon, R., Peretz, T., and Vlodavsky, I. 1996. Sulfate moieties in the subendothelial extracellular matrix are involved in basic fibroblast growth factor sequestration, dimerization, and stimulation of cell proliferation. *J. Biol. Chem.* 271:4879-4886.
9. Moscatelli, D., Flaumenhaft, R., and Saksela, O. 1991. Interaction of basic fibroblast growth factor with extracellular matrix and receptors. *Ann. NY Acad. Sci.* 638: 177-181.

10. Renko, M., Quarto, N., Morimoto, T., and Ritkin, D. B. 1990. Nuclear and cytoplasmic localization of different basic fibroblast growth factor species. *J Cell. Physiol.* 144: 108-114.
11. Amalric, F., VBaldin, V., Bosc-Bieme, I., Bugler, B., Couderc, B., Guyader, M., Patry, V., Prats, H., Roman, A. M., and Bouche, G. 1991. Nuclear translocation of basic fibroblast growth factor. *Ann. NY A cad. Sci.* 638:127-138.
12. Rifkin, D. B., Moscatelli, D., Roghani, M., Nagano, Y., Quarto, N., Klein, S., and Bikfalvi, A. 1994. Studies on FGF-2: nuclear localization and function of high molecular weight fonl1s and receptor binding in the absence of heparin. *Mol. Reprod. Dev.* 39:102-105.
13. Piotrowicz, R. S., Martin, J. L., Dillmann, W. H., and Levin, E. G. 1997. The 27-kDa heat shock protein facilitates basic fibroblast growth factor release from endothelial cells. *J: Bio/. Chem.* 272:7042-7047.

---

What is claimed is:

1. An isolated polypeptide comprising the polypeptide sequence shown by SEQ ID NO: 2, wherein said polypeptide has at least one of anti-angiogenic, tumor-suppressive, or anti-migratory activity, but does not have stimulation of cell proliferation activity.

2. A pharmaceutical composition comprising a pharmaceutically effective amount of the polypeptide of claim 1.

3. The Pharmaceutical composition of claim 2, wherein said pharmaceutical composition further comprises one or more pharmaceutically acceptable carriers.

4. A fusion protein having at least two components, wherein one component of said fusion protein comprises the polypeptide of claim 1.

5. A dimer, wherein one monomer is the polypeptide of claim 1.

6. A multimer, wherein at least one monomer is the polypeptide of claim 1.

7. The polypeptide of claim 1, wherein said polypeptide is immobilized to a solid support or carrier.

8. An isolated polypeptide comprising an amino acid sequence that differs from the amino acid sequence of SEQ ID NO: 2 by one or more conservative amino acid substitutions, wherein said polypeptide has at least one of anti-angiogenic, tumor-suppressive, or anti-migratory activity, but does not have stimulation of cell proliferation activity.

* * * * *